US006693070B1

(12) United States Patent
Cheung et al.

(10) Patent No.: US 6,693,070 B1
(45) Date of Patent: Feb. 17, 2004

(54) HARD SURFACE CLEANING AND DISINFECTING COMPOSITION

(75) Inventors: Tak Wai Cheung, Bridgewater, NJ (US); Dennis Thomas Smialowicz, West Milford, NJ (US)

(73) Assignee: Reckitt Benckiser Inc., Wayne, NJ (US)

( * ) Notice: Subject to any disclaimer, the term of this patent is extended or adjusted under 35 U.S.C. 154(b) by 0 days.

(21) Appl. No.: 09/913,455

(22) PCT Filed: Feb. 14, 2000

(86) PCT No.: PCT/GB00/00464
§ 371 (c)(1),
(2), (4) Date: Nov. 13, 2001

(87) PCT Pub. No.: WO00/49127

PCT Pub. Date: Aug. 24, 2000

(30) Foreign Application Priority Data

Feb. 17, 1999 (GB) .............................................. 9903478

(51) Int. Cl.⁷ .............................. C11D 1/62; C11D 3/48
(52) U.S. Cl. ........................ 510/384; 510/235; 510/237; 510/238; 510/382; 510/384; 510/391; 510/432; 510/504; 510/506
(58) Field of Search ................................ 510/235, 237, 510/238, 382, 384, 391, 432, 504, 506

(56) References Cited

U.S. PATENT DOCUMENTS

| 4,540,505 A | | 9/1985 | Frazier ........................ 252/106 |
| 4,895,667 A | * | 1/1990 | Fox et al. ..................... 252/8.8 |
| 5,629,280 A | | 5/1997 | Richter et al. ............... 510/463 |
| 5,962,388 A | * | 10/1999 | Sherry et al. ............... 510/238 |
| 6,358,900 B1 | * | 3/2002 | Wigley et al. .............. 510/180 |

FOREIGN PATENT DOCUMENTS

| DE | 195 15 286 A1 | 10/1997 | .......... A01N/37/44 |
| EP | 0 111 965 A2 | 6/1984 | ............ C11D/1/40 |
| EP | 0 478 445 A1 | 4/1992 | ............ C11D/3/48 |
| GB | 718050 | 11/1954 | ...................... 81/1 |
| GB | 882860 | 11/1961 | ...................... 81/1 |
| GB | 2 075 043 A | 11/1981 | .......... C11D/1/835 |
| GB | 2 302 030 A | 1/1997 | ............ A62B/9/00 |
| GB | 2 304 728 A | 3/1997 | ............ C11D/1/65 |
| GB | 2 307 915 | 6/1997 | ............ C11D/3/48 |
| GB | 2 320 030 A | 6/1998 | ............ C11D/1/94 |

* cited by examiner

Primary Examiner—Charles Boyer
(74) Attorney, Agent, or Firm—Fish & Richardson P.C.

(57) ABSTRACT

Hard surface cleaning and disinfecting compositions comprise a synergistic combination of a quaternary ammonium germicide and an alkoxylated quaternary ammonium compound. Optional ingredients include additional detersive surfactants and/or organic solvents.

12 Claims, No Drawings

HARD SURFACE CLEANING AND DISINFECTING COMPOSITION

BACKGROUND OF THE INVENTION

The present invention relates to hard surface cleaning and disinfecting compositions which comprise a synergistic combination of a quaternary ammonium compound and an alkoxylated quaternary ammonium compound.

The prior art has suggested many aqueous compositions which are directed to provide a cleaning or disinfecting benefit to such hard surfaces. These compositions predominantly are aqueous preparations which include one or more detersive surfactants, one or more organic solvents and, in minor amounts, conventional additives included to enhance the attractiveness of the product, typically fragrances and coloring agents. Certain of these also include one or more constituents which provide a primary disinfecting benefit to the aqueous preparations.

While these known-art compositions may provide advantages, there is a continuing need for such hard surface treatment compositions which include reduced amounts of active constituents, and which minimize or eliminate the amounts of organic solvents which need be present in such compositions. It is yet a further object of the invention to provide a readily pourable and readily pumpable cleaning composition which features the benefits described above.

It is a further object of the invention to provide a process for cleaning or sanitization of hard surfaces, which process comprises the step of: providing the composition as outlined above, and applying an effective amount to a hard surface requiring such treatment.

These and other objects of the invention will be more apparent from a reading of the specification and of the claims attached.

SUMMARY OF THE INVENTION

According to a first aspect of the invention there is provided a hard surface cleaning and disinfecting composition which comprises (preferably, consisting essentially of) the following constituents:

(a) a germicidal constituent which provides a primary sanitizing benefit, preferably a quaternary ammonium compound;

(b) an alkoxylated quaternary ammonium compound;

(c) optionally, one or more detersive surfactants particularly selected from carboxylate, nonionic, cationic and amphoteric surfactants;

(d) optionally, one or more organic solvents; and (e) a major proportion of water.

The compositions described above may include one or more further conventional optional constituents such as: pH buffering agents, perfumes, perfume carriers, colorants, hydrotropes, germicides, fungicides, anti-oxidants, anti-corrosion agents, and the like.

Preferred compositions according to the invention are largely aqueous, and are readily pourable and pumpable when packaged from a manually operable pump, such as a 'trigger spray' dispenser. The preferred compositions of the invention feature good cleaning, disinfection of hard surfaces and little or not buildup of residue on treated hard surfaces.

According to a second aspect of the invention, there is provided a hard surface cleaning and disinfecting composition which comprises (preferably, consists essentially of) the following constituents:

(a) a germicidal constituent which provides a primary sanitizing benefit, preferably a quaternary ammonium compound;

(b) an alkoxylated quaternary ammonium compound;

(c) one or more detersive surfactants particularly selected from carboxylate, nonionic, cationic and amphoteric surfactants; and (e) a major proportion of water;

characterized in that the composition is essentially free of (d) one or more organic solvents, such as water soluble alcohols, ethers, and glycol ethers. These compositions may include one or more further conventional optional constituents such as: pH buffering agents, perfumes, perfume carriers, colorants, hydrotropes, germicides, fungicides, anti-oxidants, anti-corrosion agents, and the like.

According to a third aspect of the invention, there is provided a hard surface cleaning and disinfecting composition which comprises (preferably, consists essentially of) the following constituents:

(a) a germicidal constituent which provides a primary sanitizing benefit, preferably a quaternary ammonium compound;

(b) an alkoxylated quaternary ammonium compound;

(d) one or more organic solvents; and (e) a major proportion of water;

characterized in that the composition is essentially free of (c) one or more detersive surfactants particularly selected from carboxylate, nonionic, cationic and amphoteric surfactants. The compositions may include one or more further conventional optional constituents such as: pH buffering agents, perfumes, perfume carriers, colorants, hydrotropes, germicides, fungicides, anti-oxidants, anti-corrosion agents, and the like.

In accordance with a fourth aspect of the invention, there is provided a hard surface cleaning and disinfecting composition which comprises (preferably, consists essentially of) the following constituents:

(a) a germicidal constituent which provides a primary sanitizing benefit, preferably a quaternary ammonium compound;

(b) an alkoxylated quaternary ammonium compound; and (e) a major proportion of water;

wherein the compositions are essentially free of (c) detersive surfactants, particularly carboxylate, nonionic, cationic and amphoteric surfactants, as well as being essentially free of (d) organic solvents. The compositions described above may include one or more further conventional optional constituents such as: pH buffering agents, perfumes, perfume carriers, colorants, hydrotropes, germicides, fungicides, anti-oxidants, anti-corrosion agents, and the like.

DETAILED DISCLOSURE

The inventive compositions necessarily include (a) at least one germicidal constituent which provides a primary sanitizing benefit to the compositions.

Particularly preferred for use as the (a) germicidal constituent is at least one cationic surfactant which is found to provide a broad antibacterial or sanitizing function. Any cationic surfactant which satisfies these requirements may be used and is considered to be within the scope of the present invention, and mixtures of two or more cationic surface active agents may also be used. Cationic surfactants are well known, and useful cationic surfactants may be one or more of those described for example in *McCutcheon's Detergents and Emulsifiers*, North American Edition, 1982;

Kirk-Othmer, *Encyclopedia of Chemical Technology*, 3rd Ed., Vol. 22, pp. 346–387, the contents of which are herein incorporated by reference.

Examples of preferred cationic surfactant compositions useful in the practice of the instant invention are those which provide a germicidal effect to the concentrated compositions, and especially preferred are quaternary ammonium compounds and salts thereof, which may be characterized by the general structural formula:

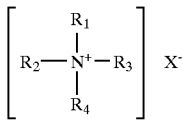

where each of $R_1$, $R_2$, $R_3$ and $R_4$ is an alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons, usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

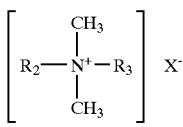

wherein:

$R_2$ and $R_3$ are the same or different $C_8$–$C_{12}$alkyl;

or $R_2$ is $C_{12-16}$alkyl, $C_{8-18}$alkylethoxy, $C_{8-18}$alkylphenolethoxy and $R_3$ is benzyl; and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Particularly useful quaternary germicides include which are described as being a blend of alkyl dimethyl benzyl ammonium chlorides; BARDAC® 205M, BARDAC® 2050, BARDAC® 2080, BARDAC® 2250, BTC® 812, BTC® 818 and BTC® 1010, which are described as being based on dialkyl($C_8$–$C_{10}$)dimethyl ammonium chloride; BARDAC® 2250 and BARDAC® 2280 or BTC® 1010, which are described as being a composition which includes didecyl dimethyl ammonium chloride; BARDAC® LF and BARDACO LF 80, which are described as being based on dioctyl dimethyl ammonium chloride; BARQUAT® MB-50, BARQUAT® MB-80, BARQUAT® MX-50, BARQUAT® MX-80, BARQUAT® OJ-50, BARQUAT® OJ-80, BARDAC® 208M, HYAMINE® 3500, HYAMINE® 3500-NF, BTC® 50, BTC® 824, BTC® 835, BTC® 885, BTC® 2565, BTC® 2658, BTC® 8248 or BTC® 8358 each described as being based on alkyl dimethyl benzyl ammonium chloride (benzalkonium chloride); BARQUAT® 4250, BARQUAT® 4280, BARQUAT® 4250Z, BARQUAT® 4280Z, BTC® 471, BTC® 2125, or BTC® 2125M, each described as being a composition based on alkyldimethylbenzyl ammonium chloride and/or alkyldimethylethylbenzyl ammonium chloride; BARQUAT® MS-100 or BTC® 324-P-100, each described as being based on myristyldimethylbenzyl ammonium chloride; HYAMINE® 2389, described as being based on methyldodecylbenzyl ammonium chloride and/or methyldodecylxylene-bis-trimethyl ammonium chloride; HYAMINE® 1622, described as being an aqueous solution of benzethonium chloride; as well as BARQUAT® 1552 or BTC® 776, described as being based on alkyl dimethyl benzyl ammonium chloride and/or dialkyl methyl benzyl ammonium chloride, BARQUAT® 50-MAB, described as being based on alkyldimethylethyl ammonium bromide and LONZABAC®-12.100, described as being based on an alkyl tertiary amine. (Each of these recited materials are presently commercially available from Lonza, Inc., Fairlawn, N.J. and/or from Stepan Co., Northfield Ill.)

The germidical constituent may be present in any effective amount, but generally need not be present in amounts in excess of about 10% wt. based on the total weight of the composition. The preferred germicidal cationic surfactant(s) may be present in the concentrated liquid disinfectant compositions in amounts of from about 0.001% by weight to up to about 10% by weight, preferably about 0.01–8% by weight, more preferably in amount of between 0.5–6% by weight, and most preferably from 2–4% by weight. It is particularly advantageous that the preferred germicidal cationic surfactant(s) are present in amounts of at least 200 parts per million (ppm), preferably in amounts of 200–700 ppm, more preferably in amounts of from 250–500 ppm, and very especially in amount of from 300–500 ppm.

The inventive compositions necessarily include (b) at least one alkoxylated quaternary ammonium compound. This alkoxylated quaternary ammonium compound are selected to differ from the quaternary ammonium compounds discussed above. These (b) alkoxylated quaternary ammonium compounds include materials which are per se, known to the art.

Particularly useful alkoxylated quaternary ammonium compounds include those which may be represented by the general structure:

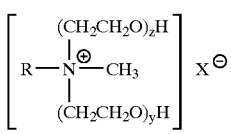

wherein:

R is a $C_8$–$C_{24}$ alkyl group;

z and y are individually integer values of from 1–14, inclusive, but are most preferably selected to that z+y=2–15, and in certain particularly preferred embodiments z+y=2 or 15; and X may be any counterion, but is desirably Cl or $NO_3$.

Exemplary materials include ETHOQUAD 18/12 described to be octadecylmethyl [ethoxylated (2)]-ammonium chloride; ETHOQUAD 18/25, described to be octadecyl methyl [ethoxylated (15)] ammonium chloride, ETHOQUAD C/25, described to be coco methyl [ethoxylated (15)] ammonium chloride, ETHOQUAD C/12, described to be coco methyl [ethoxylated (2)] ammonium chloride; ETHOQUAD C/12 Nitrate, described to be coco methyl [ethoxylated (2)] ammonium nitrate; ETHOQUAD O/25, described to be oleyl methyl [ethoxylated (15)] ammonium chloride; ETHOQUAD O/12 described to be oleyl methyl [ethoxylated (2)] ammonium chloride; as well as ETHOQUAD T/12 described to be tallow alkyl methyl [ethoxylated (2)] ammonium chloride.

Further exemplary materials include Q-18-15 described to be octadecyl poly(15)oxyethylene methyl ammonium chloride, and Q-C-15, described to be coco poly(15) oxyethylene methyl ammonium chloride (both of which are available from Tomah Inc.); as well as VARIQUAT K-1215, a methyl bis-(polyethoxy ethanol) coco ammonium chloride, with an 15 ethoxy groups; ADOGEN 66, an ethyl bis-(polyethoxy ethanol) tallow ammonium chloride, having 15 ethoxy groups; VARISOFT 5TD, an ethoxylated di ($C_{12}$–$C_{18}$) alkyl methyl ammonium chloride, with 5 ethoxy groups; REWOQUAT CPEM, a coco pentaethoxy methyl ammonium methosulfate, with 5 ethoxy groups, An exemplary and particularly preferred alkoxylated quaternary ammonium compound is commercially available as ETHOQUAD 18/25 (ex. AKZO Corp.). Other particularly preferred compounds are described with reference to the Examples below.

According to the second aspect of the invention, the compositions necessarily include (c) one or more surfactants which provide a further detersive benefit to the compositions.

Useful surfactants which provide a further detersive benefit which may be present in the inventive compositions include detersive surfactants particularly selected from carboxylate, nonionic, cationic and amphoteric surfactants.

Suitable nonionic surfactants include, inter alia, condensation products of alkylene oxide groups with an organic hydrophobic compound, such as an aliphatic compound or with an alkyl aromatic compound. The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic detergent. Further, the length of the polyethenoxy hydrophobic and hydrophilic elements may be varied to adjust these properties.

One example of such a nonionic surfactant is the condensation product of one mole of an alkyl phenol having an alkyl group containing from 6 to 12 carbon atoms with from about 5 to 25 moles of an alkylene oxide. Another example of such a nonionic surfactant is the condensation product of one mole of an aliphatic alcohol which may be a primary, secondary or tertiary alcohol having from 6 to 18 carbon atoms with from 1 to about 10 moles of alkylene oxide. Preferred alkylene oxides are ethylene oxides or propylene oxides which may be present singly, or may be both present.

Preferred nonionic surfactants include primary and secondary linear and branched alcohol ethoxylates, such as those based on C6 to C18 alcohols which further include an average of from 2 to 80 moles of ethoxylation per mole of alcohol. Particularly preferred nonionic surfactants are $C_{11}$ linear primary alcohol ethoxylates averaging about 9 moles of ethylene oxide per mole of alcohol. These surfactants are available, for example, under the commercial name of Neodol 1-9, (from Shell Chemical Company, Houston, Tex.), or in the Genapol® series of linear alcohol ethoxylates, particularly Genapol® 26-L-60 or Genapol® 26-L-80 (from Clariant Corp., Charlotte, N.C.).

A further particularly useful and preferred alcohol ethoxylate is Genapol® UD-079 which is described to be a C11 linear alcohol condensed with 7 moles of ethylene oxide to form a nonionic surfactant.

It is to be understood that nonionic surfactants other than those described above may also be used. By way of illustration, and not by way of limitation, examples include secondary C12 to C15 alcohol ethoxylates, including those which have from about 3 to about 10 moles of ethoxylation. Such are available in the Tergitol® series of nonionic surfactants (Union Carbide Corp., Danbury, Conn.), particularly those in the Tergitol® "15-S-" series. Further exemplary nonionic surfactants include linear primary C11 to C15 alcohol ethoxylates, including those which have from about 3 to about 10 moles of ethoxylation. Such are available in the Neodol® series of nonionic surfactants (Shell Chemical Co.)

A further class of nonionic surfactants which may find use in the present inventive compositions include ethoxylated octyl and nonyl phenols include those having one of the following general structural formulas:

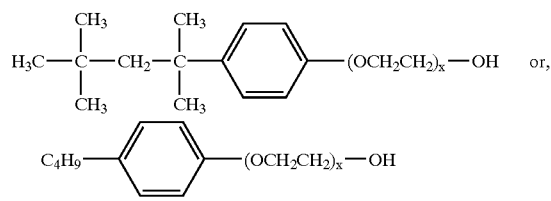

in which the $C_9H_{19}$ group in the latter formula is a mixture of branched chained isomers, and x indicates an average number of ethoxy units in the side chain. Particularly suitable non-ionic ethoxylated octyl and nonyl phenols include those having from about 7 to about 13 ethoxy units. Such compounds are commercially available under the trade name Triton® X (Union Carbide, Danbury Conn.), as well as under the tradename Igepal® (Rhone-Poulenc, Princeton, N.J.). One exemplary and particularly preferred nonylphenol ethoxylate is Igepal® CO-630.

One useful class of surfactants include amine oxide compounds. Exemplary useful amine oxide compounds may be defined as one or more of the following of the four general classes:

(1) Alkyl di (lower alkyl) amine oxides in which the alkyl group has about 6–24, and preferably 8–18 carbon atoms, and can be straight or branched chain, saturated or unsaturated. The lower alkyl groups include between 1 and 7 carbon atoms, but preferably each include 1–3 carbon atoms. Examples include octyl dimethyl amine oxide, lauryl dimethyl amine oxide, myristyl dimethyl amine oxide, and those in which the alkyl group is a mixture of different amine oxides, such as dimethyl cocoamine oxide, dimethyl (hydrogenated tallow) amine oxide, and myristyl/palmityl dimethyl amine oxide;

(2) Alkyl di (hydroxy lower alkyl) amine oxides in which the alkyl group has about 6–22, and preferably 8–18 carbon atoms, and can be straight or branched chain, saturated or unsaturated. Examples include bis-(2-hydroxyethyl) cocoamine oxide, bis-(2-hydroxyethyl) tallowamine oxide, and bis-(2-hydroxyethyl) stearylamine oxide;

(3) Alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and (4) Alkylmorpholine oxides in which the alkyl group has about 10–20, and preferably 12–16 carbon atoms, and can be straight or branched chain, saturated or unsaturated.

While these amine oxides recited above may be used, preferred are amine oxides which may be represented by the following structural representation:

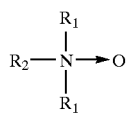

wherein
each $R_1$ independently is a straight chained $C_1$–$C_4$ alkyl group, preferably both $R_1$ being methyl groups; and,
$R_2$ is a straight chained $C_6$–$C_{22}$ alkyl group, preferably is $C_6$–$C_{16}$ alkyl group, most preferably is a $C_{8-10}$ alkyl group, especially a $C_8$ alkyl group;

Each of the alkyl groups may be linear or branched, but preferably are linear groups. Most preferably the amine oxide constituent is lauryl dimethyl amine oxide. Technical grade mixtures of two or more amine oxides may be used, wherein amine oxides of varying chains of the R2 group are present. Preferably, the amine oxides used in the present invention include R2 groups which comprise at least 50% wt., preferably at least 75% wt. of $C_8$ alkyl group.

Exemplary and preferred amine oxide compounds include N-alkyl dimethyl amine oxides, particularly octyl dimethyl amine oxides as well as lauryl dimethyl amine oxide. These amine oxide compounds are available as surfactants from McIntyre Group Ltd. under the name Mackamine® C-8, which is described as a 40% by weight active solution of octyl dimethyl amine oxide, as well as from Stepan Co., under the tradename Ammonyx® LO, which is described to be as a 30% wt. active solution of lauryl dimethyl amine oxide.

A further class of surfactants which may be advantageously included in the inventive compositions are alkoxy block copolymers, and in particular, compounds based on ethoxy/propoxy block copolymers. Polymeric alkylene oxide block copolymers include nonionic surfactants in which the major portion of the molecule is made up of block polymeric $C_2$–$C_4$ alkylene oxides. Such nonionic surfactants, while preferably built up from an alkylene oxide chain starting group, can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

where
EO represents ethylene oxide,
PO represents propylene oxide,
y equals at least 15,
$(EO)_{x+z}$ equals 20 to 50% of the total weight of said compounds, and,
the total molecular weight is preferably in the range of about 2000 to 15,000.

Another group of nonionic surfactants appropriate for use in the new compositions can be represented by the formula (B):

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000–5000.

Still further useful nonionic surfactants containing polymeric butoxy (BO) groups can be represented by formula (C) as follows:

wherein
R is an alkyl group containing 1 to 20 carbon atoms,
n is about 5–15 and x is about 5–15.

Also useful as the nonionic block copolymer surfactants, which also include polymeric butoxy groups, are those which may be represented by the following formula (D):

wherein
n is about 5–15, preferably about 15,
x is about 5–15, preferably about 15, and
y is about 5–15, preferably about 15.

Still further useful nonionic block copolymer surfactants include ethoxylated derivatives of propoxylated ethylene diamine, which may be represented by the following formula:

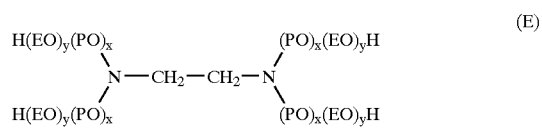

where (EO) represents ethoxy,
(PO) represents propoxy,
the amount of (PO)$_x$ is such as to provide a molecular weight prior to ethoxylation of about 300 to 7500, and the amount of (EO)$_y$ is such as to provide about 20% to 90% of the total weight of said compound.

Of these, the most preferred are those which are represented by formula (A) above; specific examples of which include those materials presently commercially available under the tradename "Pluronic®", and in particular the Pluronic® F series, Pluronic® L series, Pluronic® P series, as well as in the Pluronic® R series, each of which are generally described to be block copolymers of propylene oxide and ethylene oxide. Generally those of the Pluronic® L series and the Pluronic® R series are preferred as these are supplied in liquid form by the manufacturer and are readily formulated into the present inventive compositions. These are also available in a wide range of HLB values, and those having HLB values in the range of 1.0–23.0 may be used, although those with intermediate HLB values such as from about 12.0–18.0 are found to be particularly advantageous. These materials are presently commercially available from BASF AG (Ludwigshafen, Germany) as well as from BASF Corp. (Mt. Olive Township, N.J.).

A further class of surfactants which may be advantageously included in the inventive compositions are carboxylates, particularly one or more alkylpolyoxycarboxylates including alkyletherpolyoxycarboxylates, or alkylarylpolycarboxylates. Exemplary alkylpolyoxycarboxylates and alkylarylpolycarboxylates include alkyl- and alkylaryl-carboxylates which include those which may be represented by the general formula:

wherein R is a straight or branched hydrocarbon chain containing from about 9 to 21 carbon atoms, and which may also include an aromatic ring, especially a phenyl group as part of the hydrocarbon chain, and M is a metal or ammonium ion.

Further examples of particularly useful carboxylate surfactants include compounds according to the formula:

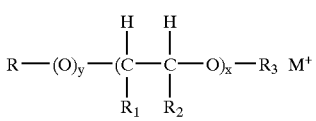

where:
R is a C$_4$–C$_{22}$ linear or branched alkyl group which may optionally include at least one aryl group, preferably C$_8$–C$_{15}$ linear or branched alkyl group which may include at least one aryl group, and yet more preferably a C$_{12-15}$ linear or branched alkyl group which may include at least one aryl group;
x is an integer from 1 to 24,
y is 0 or 1,
each of R$_1$, R$_2$ and R$_3$ is a group selected from H, lower alkyl radicals including methyl and ethyl radicals, carboxylate radicals including acetate and propionate radicals, succinate radicals, hydroxysuccinate radicals, or mixtures thereof wherein at least one R$_1$, R$_2$ or R$_3$ is a carboxylate radical; and,
M$^+$ is a counterion including an alkali metal counterion (i.e., sodium, potassium) or ammonium counterion.
Free acid forms of the alkylethercarboxylate compounds noted above may also be used.

Examples of such presently available commercial preparations include SURFINE WLG (Finetex Inc., Elmwood Park N.J.), SANDOPAN DTC (Clariant Chem.Co., Charlotte N.C.) in salt forms, and in free acid forms include those marketed under the tradename NEODOX (Shell Chemical Co., Houston Tex.). One particularly preferred carboxylate is one which is represented by the formula:

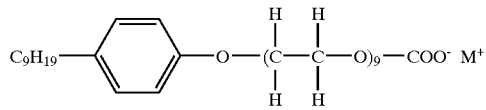

Such a material is presently commercially available under the tradename Emcol®, and specifically as Emcol® CNP-110.

Other useful exemplary nonionic block copolymers based on a polymeric ethoxy/propoxy units which may also be used include those presently commercially available in the Poly-Tergent® E, and Poly-Tergent® P series of materials from Olin Chemicals Corp., (Stamford Conn.). These are described to be nonionic surfactants based on ethoxy/propoxy block copolymers, conveniently available in a liquid form from its supplier.

It is to be understood that these nonionic surfactants based on polymeric alkylene oxide block copolymers may be used singly or in mixtures of two or more such compounds.

Amphoteric surfactants, also known as zwitterionic surfactants, contain both cationic and anionic hydrophilic groups on the same molecule at a relatively wide range of pHs. The typical cationic group is a quaternary ammonium group, although other positively charged groups, like sulfonium groups, can also be used. The typical anionic hydrophilic groups are carboxylates and sulfonates, although other groups like sulfates, etc., can be used. Amphoteric surfactants also include betaine and sulphobetaine surfactants, derivatives thereof, and mixtures thereof wherein the molecule contains both basic and acidic groups which form an inner salt giving the molecule both cationic and anionic hydrophilic groups over a broad range of pH values, as well as mono- and diacetates, glycinates, imidazolines and their derivatives, isethionates, mono- and diproprionates, hydroxy sultaines, and taurates.

When the compositions of the present invention contain one or more further detersive surfactants, these may be present in any amount which is found to provide a beneficial detersive effect. Generally, these one or more further detersive surfactants do not comprise more than 12% wt. (on an actives weight basis) of the inventive compositions. When included such one or more further detersive surfactants are advantageously present in an amount from 0.001–10% wt., preferably are present from 0.01–8% wt., but still more preferably are included in amounts of from 0.1–8% wt.

According to the third aspect of the invention, the compositions necessarily include (d) one or more organic solvents.

Exemplary organic solvents which may be included in the inventive compositions include those which are at least partially water-miscible such as alcohols, water-miscible ethers (e.g. diethylene glycol diethylether, diethylene glycol dimethylether, propylent glycol dimethylether), water-miscible glycol ethers (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethyleneglycol or propylene glycol (e.g. propylene glycol monomethyl ether acetate) all commercially available from Union Carbide (Danbury, Conn.), Dow Chemical Co. (Midland, Mich.) or Hoescht (Germany). Mixtures of several organic solvents can also be used.

Preferred as solvents in this invention are the glycol ethers having the general structure $R_a$—O—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from one to ten glycol monomer units. Preferred are glycol ethers having one to five glycol monomer units. These are $C_3$–$C_{20}$ glycol ethers. Examples of more preferred solvents include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenyl ether, and mixtures thereof.

The compositions are largely aqueous in nature, and comprise as a further necessary constituent (e) water. Water is added to order to provide to 100% by weight of the compositions of the invention. The water may be tap water, but is preferably distilled and is most preferably deionized water. If the water is tap water, it is preferably substantially free of any undesirable impurities such as organics or inorganics, especially mineral salts which are present in hard water which may thus undesirably interfere with the operation of the constituents present in the aqueous compositions according to the invention.

As discussed previously, the inventive compositions may comprise one or more conventional optional additives. By way of non-limiting example, these include: pH adjusting agents and pH buffers including organic and inorganic salts; non-aqueous solvents, perfumes, perfume carriers, optical brighteners, coloring agents such as dyes and pigments, opacifying agents, hydrotropes, antifoaming agents, viscosity modifying agents such as thickeners, enzymes, antispotting agents, anti-oxidants, anti-corrosion agents as well as others not specifically elucidated here. These ingredients may be present in any combinations and in any suitable amount that is sufficient for imparting the desired properties to the compositions. These one or more conventional additives, when present, should be present in minor amounts, preferably in total comprise less than about 5% by weight (on an active weight basis) of the compositions, and desirably less than about 3% wt.

Such materials described above are known to the art, including those described in *McCutcheon's Emulsifiers and Detergents* (Vol.1), *McCutcheon's Functional Materials* (Vol. 2), North American Edition, 1991; Kirk-Othmer, *Encyclopedia of Chemical Technology*, 3rd Ed., Vol. 22, the contents of which are herein incorporated by reference For any particular composition, any optional constituents should be compatible with the other ingredients present.

The aqueous compositions according to the invention are desirably provided as a ready to use product which may be directly applied to a hard surface. Hard surfaces which are to be particularly denoted are lavatory fixtures, lavatory appliances (toilets, bidets, shower stalls, bathtubs and bathing appliances), wall and flooring surfaces especially those which include refractory materials and the like. Further hard surfaces which are particularly denoted are those associated with kitchen environments and other environments associated with food preparation. Hard surfaces also include those associated with hospital environments, medical laboratories and medical treatment environments. Such hard surfaces described above are to be understood as being recited by way of illustration and not be way of limitation.

The composition according to the invention is ideally suited for use in a consumer "spray and wipe" application. In such an application, the consumer generally applies an effective amount of the cleaning composition using the pump and within a few moments thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposits after which it may then be wiped off, rinsed off, or otherwise removed. For particularly heavy deposits of such undesired stains, multiple applications may also be used. Where thorough disinfection is a primary consideration, it may be desired to apply the inventive compositions to the hard surface being treated and to permit the composition to remain on the hard surface for several minutes (2–10 min.) prior to rinsing or wiping the composition from the hard surface. It is also contemplated that the inventive compositions be applied to a hard surface without subsequently wiping or is rinsing the treated hard surface.

In a yet a further embodiment, the product according to the invention may be formulated so that it may be useful in conjunction with a "aerosol" type product wherein it is discharged from a pressurized aerosol container. Known art propellants such as liquid propellants based on chlorofluorocarbons or propellants of the non-liquid form, i.e., pressurized gases, including carbon dioxide, air, nitrogen, as well as others, may be used, even though it is realized that the chlorofluorocarbons are no longer generally used due to environmental considerations. In such an application, the cleaning composition is dispensed by activating the release nozzle of said aerosol type container onto the stain and/or stain area, and in accordance with a manner as above-described a stain is treated and removed.

Whereas the compositions of the present invention are intended to be used in the types of liquid forms described, nothing in this specification shall be understood as to limit the use of the composition according to the invention with a further amount of water to form a cleaning solution therefrom. In such a proposed diluted cleaning solution, the greater the proportion of water added to form said cleaning dilution will, the greater may be the reduction of the rate and/or efficacy of the thus formed cleaning solution. Accordingly, longer residence times upon the stain to effect their loosening and/or the useage of greater amounts may be necessitated. Conversely, nothing in the specification shall be also understood to limit the forming of a "super-concentrated" cleaning composition based upon the composition described above. Such a super-concentrated ingredient composition is essentially the same as the cleaning compositions described above except in that they include a lesser amount of water.

The following examples below illustrate exemplary and preferred formulations of the concentrate composition according to the instant invention. It is to be understood that these examples are presented by means of illustration only and that further useful formulations fall within the scope of this invention and the claims may be readily produced by one skilled in the art and not deviate from the scope and spirit of the invention.

Throughout this specification and in the accompanying claims, weight percents of any constituent are to be understood as the weight percent of the active portion of the referenced constituent, unless otherwise indicated.

EXAMPLES

The following examples illustrate the formulation and performance of various compositions of the invention, as well as certain particularly preferred embodiments of the invention.

Exemplary formulations illustrating certain preferred embodiments of the inventive compositions and described in more detail in Table 1 below were formulated generally in accordance with the following protocol. The weight percentages indicated the "as supplied" weights of the named constituent.

Into a suitably sized vessel, a measured amount of water was provided after which the constituents were added in no specific or uniform sequence, which indicated that the order of addition of the constituents was not critical. All of the constituents were supplied at room temperature, and any remaining amount of water was added thereafter. Certain of the nonionic surfactants, if gels at room temperature, were first preheated to render them pourable liquids prior to addition and mixing. Mixing of the constituents was achieved by the use of a mechanical stirrer with a small diameter propeller at the end of its rotating shaft. Mixing, which generally lasted from 5 minutes to 120 minutes was maintained until the particular exemplary formulation appeared to be homogeneous. The exemplary compositions were readily pourable, and retained well mixed characteristics (i.e., stable mixtures) upon standing for extended periods. The compositions of the example formulations are listed on Table 1. Certain comparative examples are also described on Table 1; these are identified as "C" followed by an integer number.

TABLE 1

|  | C1 | C2 | Ex.1 | Ex.2 |
|---|---|---|---|---|
| BTC-8358 (80%) | 3.6 | — | 3.6 | 3.6 |
| ETHOQUAD 18/25 (95%) | — | 2.12 | 0.68 | 2.12 |
| di water | q.s. | q.s. | q.s. | q.s. |

As is indicated, to all of the formulations of Table 1 was added sufficient deionized water in "quantum sufficient" to provide 100 parts by weight of a particular formulation.

The identity of the constituents of used to produce various formulations described herein are disclosed on Table 2, below, including the "actives" percentage of each were a constituent was not 100% wt. "actives".

TABLE 2

| BTC-8358 (80%) | alkyl dimethyl benzyl ammonium chloride (80% wt. actives) from Stepan Co. |
|---|---|
| ETHOQUAD 18/25 (95%) | octodecyl methyl [ethoxylated (15)] ammonium chloride 95% wt. actives) from Akzo-Nobel Co. |
| di water | deionized water |

Cleaning Efficacy

Certain of the compositions indicated above were diluted with water at a respective weight ratio of composition:water of 1:64. These diluted compositions were then subjected to the protocol of ASTM D-4488-89 Annex A5 for particulate soil, which evaluated the efficacy of the cleaning compositions on vinyl tile samples. The soil applied was a particulate soil sample containing natural humus, paraffin oil, used crankcase motor oil, Portland cement, silica, lampblack carbon, iron oxide, bandy black clay, stearic acid, and oleic acid. produced according to the protocol. Each of the soiled test vinyl tile samples were placed into the apparatus and the center of each tile was wetted with a 20 milliliter sample of a test formulation and allowed to stand for 1 minute. When approximately 30 seconds had elapsed, a further 50 milliliter sample was applied to the sponge (water dampened, then wrung to remove excess water) of a Gardner Abrasion Tester apparatus. Thereafter the apparatus was cycled 2, 4, 6, 8 and 10 times, which provided, respectively 4, 8, 12, 16 and 20 strokes of the sponge across the face of each of the vinyl test tiles. The reflectance values of the cleaned samples at 2, 4, 6, 8 and 10 cycles were evaluated utilizing a Minolta Chroma Meter CF-110, with Data Processor DP-100, which evaluated spectrophotomic characteristics of the sample. These readings are reported on Table 3, following.

TABLE 3

| Formulation | 2 cycles | 4 cycles | 6 cycles | 8 cycles | 10 cycles |
|---|---|---|---|---|---|
| C1 | 8.8 | 10.9 | 32.6 | 35.6 | 45.0 |
| C2 | 16.3 | 23.0 | 23.5 | 29.9 | 23.6 |
| C3 | 25.9 | 31.4 | 56.5 | 60.6 | 66.8 |
| Ex.1 | 57.4 | 62.8 | 61.7 | 66.8 | 65.4 |
| Ex.2 | 70.9 | 81.6 | 72.3 | 73.3 | 73.1 |

Comparative "C3" was a commercially available cleaning and disinfecting composition, LYSOL Disinfectant Cleaner, "Country Scent" (ex Reckitt & Colman Inc., Wayne, N.J.) which was diluted and tested in the manner described above. The composition of C3 was used as a benchmark for cleaning performance.

With respect to the results reported on Table 3 a value of "100" is indicative of a white (unsoiled) background, and a "0" value is indicative of a black background. As can be seen from the results of Table 3, the cleaning efficacy of the composition according to the invention provided superior results or were on parity with those of commercially available cleaning products. Surprisingly, as can be gleaned from the results of C1 and C2 in comparison with the results for Ex.1 and Ex.2, the inventive compositions provide unexpectedly superior cleaning particularly at 2, 4 and 6 cycles of the test. Such is unexpected, and is suggestive of a synergistic effect.

Antimicrobial Efficacy

The following inventive composition (identified as Ex. 3 below)

|  | Ex. 3 |
|---|---|
| BTC-8358 (80%) | 0.05625 |
| ETHOQUAD 18/25 (95%) | 0.05263 |
| di water | q.s. | was evaluated for antimicrobial activity using the Biomek® 2000 Laboratory Automation Workstation together with the BioWorks Operating System (available from Beckman Coulter Inc., Fullerton, Calif.). The organism tested was *Staphylococcus aureus* at a concentration of 9 logs. The Biomek simulates a microbial reduction suspension test. One part of organism suspension (*Staphylococcus aureus*) is added to 9 parts of Ex. 3 in an appropriate container. Deionized water (DI H20) was used a control. The organism and sample are then mixed thoroughly for 15 seconds. Serial tenfold dilutions are carried out in a neutralizing broth. The diluted samples are then incubated for 24–48 hours at 35–37° C. Thereafter, surviving organisms are quantified and log reduction, as a measurement of organism survivors are calculated as follows:

Log Reduction=(Log Survivors/DI H₂O Control)−(Log Survivors/Sample)

Ex. 3 had a log reduction of 4.8.

As may be seen from the results indicated above, the compositions according to the invention provide excellent cleaning benefits to hard surfaces, including hard surfaces with difficult to remove stains notwithstanding the low solids content of the inventive compositions. These advantages are further supplemented by the excellent antimicrobial efficacy of these compositions against known bacteria commonly found in bathroom, kitchen and other such advantages clearly illustrate the superior characteristics of the compositions, the cleaning and antimicrobial benefits attending its use which is not before known to the art.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

What is claimed is:

1. A hard surface cleaning and disinfecting composition, which consists of the following components:
   (a) a germicidal quaternary ammonium compound which provides a primary sanitizing benefit;
   (b) an alkoxylated quaternary ammonium compound;
   (c) optionally, one or more detersive surfactants selected from the group consisting of carboxylate, nonionic, cationic and amphoteric surfactants;
   (d) optionally, one or more organic solvents;
   (e) optionally, one or more additives selected from the group consisting of pH adjusting agents, pH buffers, perfumes, perfume carriers, optical brightners, dyes, pigments, opacifying agents, hydrotropes, anti-foaming agents, thickeners, enzymes, anti-spotting agents, anti-oxidants and anti-corrosion agents; and
   (f) water.

2. A composition according to claim 1 in which the quaternary ammonium compound is of the formula

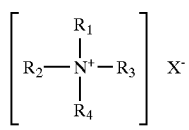

wherein
   each of $R_1$, $R_2$, $R_3$ and $R_4$ is an alkyl, aryl or alkaryl substituent having from 6 to 26 carbon atoms,
   X is a salt-forming anion which permits water solubility of said compound, and
   the cation portion of the compound has a molecular weight of at least 165, and the alkoxylated quaternary ammonium compound has the formula

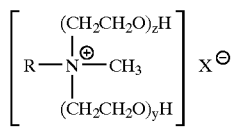

wherein

R is a $C_8$–$C_{24}$ alkyl group, z and y are individually integer values from 1 to 14, and X is a counterion.

3. A composition according to claim 2 in which the quaternary ammonium compound has the formula

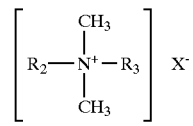

wherein
   $R_2$ and $R_3$ are the same or different and are $C_8$–$C_{12}$ alkyl, or $R_2$ is $C_{12}$–$C_{16}$ alkyl, $C_8$–$C_{18}$ alkyl ethoxy, $C_8$–$C_{18}$ alkylphenolethoxy, and $R_3$ is benzyl, and
   X is a halide or a methosulfate ion.

4. A composition according to claim 3 in which, in the quaternary ammonium compound, both $R_2$ and $R_3$ are straight chained alkyl groups.

5. A composition according to claim 3 in which the quaternary ammonium germicide component (a) is a blend of alkyldimethylbenzylammonium chlorides.

6. A composition according to claim 2 in which, in the alkoxylated quaternary ammonium compound component, z+y ranges from 2 to 15.

7. A composition according to claim 6 in which, in the alkoxylated quaternary ammonium component, X is chloride or nitrate.

8. The composition according to claim 2 which comprises one or more detersive surfactants selected from the group consisting carboxylate, nonionic, cationic and amphoteric surfactants.

9. A composition according to claim 2 which comprises one or more organic solvents selected from the group consisting of alcohols, ethers, glycol ethers, lower esters of monoethers of ethylene glycol or propylene glycol, and mixtures thereof.

10. A composition according to claim 9 in which the organic solvent is a glycol ether of the formula

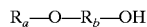

wherein $R_a$ is alkyl from of 1 to 20 carbon atoms, or aryloxy of at least 6 carbon atoms, and $R_b$ is an ether condensate of a propylene glycol and/or ethylene glycol having from 1 to 10 glycol monomer units.

11. A composition according to claim 10 in which the solvent is selected from the group consisting of propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenyl ether and mixtures thereof.

12. A composition according to claim 2 which is essentially free of component (d).

* * * * *